US00PP15821P2

(12) United States Plant Patent
Olesen et al.

(10) Patent No.: US PP15,821 P2
(45) Date of Patent: Jun. 28, 2005

(54) COMPACT FLORIBUNDA ROSE PLANT NAMED 'POULAC001'

(50) Latin Name: *Rosa hybrida*
Varietal Denomination: POULac001

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,712

(22) Filed: Mar. 29, 2004

(51) Int. Cl.[7] ..... A01H 5/00

(52) U.S. Cl. ..... Plt./150

(58) Field of Search ..... Plt./150, 149, 151

(56) References Cited

U.S. PATENT DOCUMENTS

2003/0066112 P1 * 4/2003 Olesen et al. ..... Plt./147

* cited by examiner

*Primary Examiner*—Anne Marie Grunberg
*Assistant Examiner*—June Hwu

(57) ABSTRACT

A new garden rose plant of the compact floribunda class which has abundant, red flowers and attractive foliage. This new and distinct variety has shown to be uniform and stable in the resulting generations from asexual propagation.

2 Drawing Sheets

Botanical classification: *Rosa hybrida.*
Variety denomination: 'POULac011'.

SUMMARY OF THE INVENTION

The present invention constitutes a new and distinct variety of garden rose plant which originated from a controlled crossing between a unnamed female parent plant and the male parent 'POULmax', described and illustrated in U.S. Plant patent application Ser. No. 10/192,746 dated Jul. 9, 2002. The two parents were crossed during the summer of 1992 and the resulting seeds were planted in a controlled environment in Fredensborg, Denmark. The new variety is named 'POULac011'.

The new variety may be distinguished from its unnamed female seed parent, by the following characteristic:

While the seed parent has dark red flowers, 'POULac011' has medium red flowers.

The new variety may be distinguished from its male pollen parent, 'POULmax' by the following combination of characteristics:

1. While the pollen parent 'POULmax' has a flower bud color of Red Group 46C to 47D the same characteristic of 'POULac011' is Red Group 53D.
2. While the pollen parent 'POULmax' has a petal count of 18 to 22 petals. 'POULac011' has 40 to 45 petals.
3. While the pollen parent 'POULmax' has a general tonality of Red Group 48C, 'POULac011' is Red Group 52A.

The objective of the hybridization of this rose variety was to create a new and distinct variety for garden use with unique qualities, such as:

1. Uniform and abundant medium red flowers;
2. Flower color which does not fade;
3. Vigorous, but compact growth when propagated both as a budded rose and on its own roots;
4. Disease resistance.

This combination of qualities is not present in previously available commercial cultivars of this type, known to the inventors, and distinguish 'POULac011' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'POULac011' was selected in the spring 1993 by the inventors as a single plant from the progeny of the aforementioned hybridization.

Asexual reproduction of 'POULac011' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'POULac011' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac011'. Specifically illustrated in the drawing: Sheet 1:

FIG. 1.1; Open flower, and stem showing cluster of open flowers, branching, and the attachment of leaves, buds, and peduncles;

FIG. 1.2; Flower buds at various stages of opening.

Specifically illustrated in Sheet 2:

FIG. 2.1; Sepals, receptacle, and peduncle;

FIG. 2.2; Mature leaf;

FIG. 2.3; Flower petals, detached;

FIG. 2.4; Juvenile and mature bare stem exhibiting thorns;

FIG. 2.5; Juvenile leaf exhibiting anthocyanin at leaf margins, veins, and rachis.

DETAILED DESCRIPTION OF THE VARIETY

The following is a description of 'POULac011', as observed in its growth in a field nursery in Jackson County, Oreg. Observed plants are 3 years of age. Plants were grown on *Rosa multiflora* rootstock. Color references are made using The Royal Horticultural Society (London, England) Colour Chart, 1995, except where common terms of color are used.

For a comparison, several physical characteristics of the rose variety 'POULac006', a rose variety from the same inventors described and illustrated in U.S. Plant patent application Ser. No. 10/342,702 dated Jan. 14, 2003, are compared to 'POULac011' in Chart 1.

CHART 1

| | 'POULac011' | 'POULac006' |
|---|---|---|
| General tonality | Red Group 52A to 52B with light intonations of Red-Purple Group 67B | Red Group 40A |
| Petalage | 40 to 45 petals | 35 to 40 petals |
| Flower diameter | 50 mm | 60 mm |

Parents:

*Female seed parent.*—Unnamed plant.

*Male pollen parent.*—'POULmax'.

FLOWER AND FLOWER BUD

Blooming habit: Continuous.

Flower bud:

*Size.*—Upon opening, 25 mm in length from base of receptacle to end of bud. Bud diameter is 12 mm on average.

*Bud form.*—Pointed ovoid with slightly broadened base.

*Bud color.*—As sepals unfold, petals are Red Group 53D.

*Sepals.*—Upper surface: Color: Yellow-Green Group 146C. Pubescence: Surfaces of sepals are moderately pubescent. Lower surface: Color: Yellow-Green Group 144A. Anthocyanic pigments the color of Greyed-Purple Group 183A observed. Sepal shape: Sepal apex is cirrhose. Base is flat at union with receptacle. Sepal margin: Margins have no foliaceous appendages on three of the five sepals. Stipitate glands medium to few quantity. Size: 30 mm (l)×7 mm (w).

*Receptacle.*—Surface texture: Smooth and glabrous. Shape: Urn-shaped. Size: 10 mm (h)×7 mm (w). Color: Yellow-Green Group 144A. Strong intonations of anthocyanic pigments the color of Greyed-Purple Group 183A observed.

*Pedicel.*—Surface: Smooth with stipitate glands. Length: 40 to 60 mm average length. Diameter: 2 mm. Color: Yellow-Green Group 144B. Anthocyanic pigments the color of Greyed-Red Group 181A to Greyed-Purple Group 187C observed. Strength: Strong.

*Borne.*—In clusters of 7 flower buds per stem.

Flower bloom:

*Fragrance.*—Light floral scent.

*Duration.*—The blooms have a duration on the plant of approximately 7 to 10 days. Petals fall cleanly away from plant after flowers fully mature.

*Size.*—Flower diameter is 50 mm when open. Flower depth is 23 mm on average.

*Form.*—General: Flower shape is a shallow cup with slightly overlapping petals. Shape of flower when viewed from the side: Upon opening, upper part: Flat. Upon opening, lower part: Concave. Open flower, upper part: Flat. Open flower, lower part: Concave.

Petalage: 40 to 45 petals under normal conditions, 5 to 10 of which are petaloids.

Flower color:

Upon opening, petals:

*Outermost petals.*—Outer side: Red Group 52A with intonations of Red-Purple Group 67B. Inner side: Red Group 52A to 52B.

*Innermost petals.*—Outer side: Red Group 52A with intonations of Red-Purple Group 67B. Inner side: Red Group 52A to 52B.

Upon opening, basal petal spots:

*Outermost petals.*—Outer side: White Group 155A with basal point Yellow Group 5C. Inner side: White Group 155A with basal point Yellow Group 5B.

*Innermost petals.*—Outer side: White Group 155A with center point Yellow Group 5C. Inner side: White Group 155A with basal point Yellow Group 5B.

After opening, petals:

*Outermost petals.*—Outer side: Red Group 52A with intonations of Red-Purple Group 67B. Inner side: Red Group 52A.

*Innermost petals.*—Outer side: Red Group 52A with intonations of Red-Purple Group 67B. Inner side: Red Group 52A.

After opening, basal petal spots:

*Outermost petals.*—Outer side: White Group 155A with basal point Yellow Group 5C. Inner side: White Group 155A with basal point Yellow Group 5B.

*Innermost petals.*—Outer side: White Group 155A with basal point Yellow Group 5C. Inner side: White Group 155A with basal point Yellow Group 5B.

General tonality: On Open flowers are Red Group 52A to 52B with light intonations of Red-Purple Group 67B. No change in the general tonality at the end of the 10th day.

Petals:

*Petal reflex.*—Outer petals are reflexed somewhat.

*Margin.*—Entire and uniform.

*Shape.*—Apex: Round. Base: Acute to rounded.

*Size.*—26 to 29 mm (l)×20 to 32 mm (w).

*Texture.*—Smooth.

*Thickness.*—Average to thin.

*Arrangement.*—Not formal.

Petaloids:

*Quantity.*—6 to 8.

*Color.*—Upper Surface: Red Group 52A with intonations of Red-Purple Group 67B. Lower Surface: Red Group 52A.

*Size.*—20 mm (l)×15 mm (w).

Reproductive organs:

*Pistils.*—Length: 5 mm. Quantity: 40.

*Pollen.*—None observed.

*Anthers.*—Size: 3 mm in length. Color: Greyed-Orange Group 163A. Quantity: 50 (actual count).

*Filaments.*—Color: Yellow Group 1B at base with light intonations of Greyed-Red Group 182B. Length: 5 mm.

*Stigmas.*—Even relative to the filament length and height of the anthers. Color: Yellow Group 7B.

*Styles.*—Color: Greyed-Red Group 181C. Length: 8 mm on average.

*Hips.*—None Observed in the field nursery in Jackson County Oreg.

PLANT

Plant growth: Moderate, upright to bushy. When grown as a budded field grown plant on *Rosa multiflora* understock, the average height of the plant is 40 to 60 cm and the average width is 40 cm.

Stems:

*Color.*—Young wood: Yellow-Green Group 144A to 146B. Older wood: Yellow-Green Group 144A to 146B.

*Surface texture.*—Young wood: Smooth. Older wood: Smooth.

Thorns:

*Incidence.*—11 thorns per 10 cm of stem.

*Size.*—Average length: 8 mm.

*Juvenile color.*—Greyed-Purple Group 184A.

*Mature color.*—Greyed-Yellow Group 161A.

*Shape.*—Deeply concave to concave.

Plant foliage: Normal number of leaflets on normal leaves in middle of the stem: 7 leaflets.

*Compound leaf size.*—110 mm in length by 70 mm wide on average.

*Color.*—Mature foliage: Upper surface is: Yellow-Green Group 146A. Lower surface is: Yellow-Green Group 146B. Juvenile foliage: Upper surface is: Yellow-Green Group 146B. Lower surface is: Yellow-Green Group 146C. Anthocyanin: Location: Margins and lower surfaces of juvenile foliage. Color: Greyed-Purple Group 184B.

Plant leaves and leaflets:

*Stipules.*—Size: 20 to 24 mm in length. Quantity: 2 per compound leaf. Margins: Finely serrated with medium quantity stipitate glands. Color: Yellow-Green Group 146C. Anthocyanin: Location: At margins. Color: Greyed-Red Group 183C.

*Petiole.*—Length: 45 mm. Diameter: 1.5 mm. Color: Yellow-Green Group 146B. Underneath: Prickles stipitate glands observed in low quantity.

*Rachis.*—Length: 23 to 30 mm. Color: Yellow-Green Group 146B. Underneath: Prickles stipitate glands observed in low quantity.

*Leaflet.*—Margin: Serrated. Shape: Generally ovate to round. Apex is mucronate. Base is rounded. Texture: Smooth. Thickness: Average to thick. Arrangement: Odd pinnate. Venation: Reticulate. Glossiness: Moderately glossy. Leaflet size: 30 to 35 mm (l)×22 to 31 mm (w).

Disease resistance: Above average resistance to mildew, rust, black spot, and *Botrytis* under normal growing conditions in Jackson County, Oreg.

Cold hardiness: The variety 'POULac011' has been found to be cold tolerant to USDA Cold Hardiness Zone 6.

It is claimed:

1. A new and distinct variety of rose plant of the compact floribunda rose class, substantially as herein illustrated and described as a distinct and novel rose variety due to its abundant red flowers, disease resistance, and extended period of bloom.

* * * * *

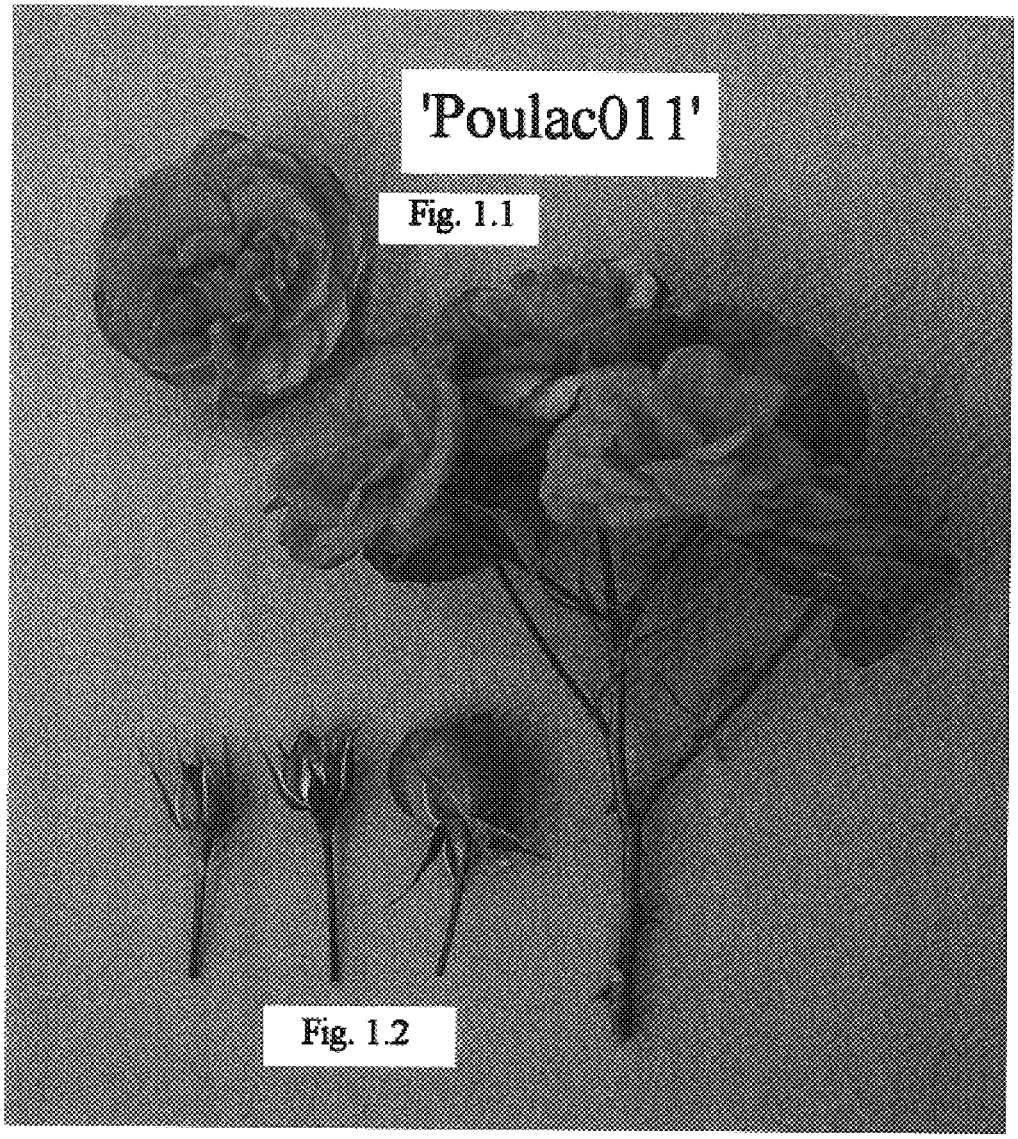
'Poulac011'
Fig. 1.1
Fig. 1.2

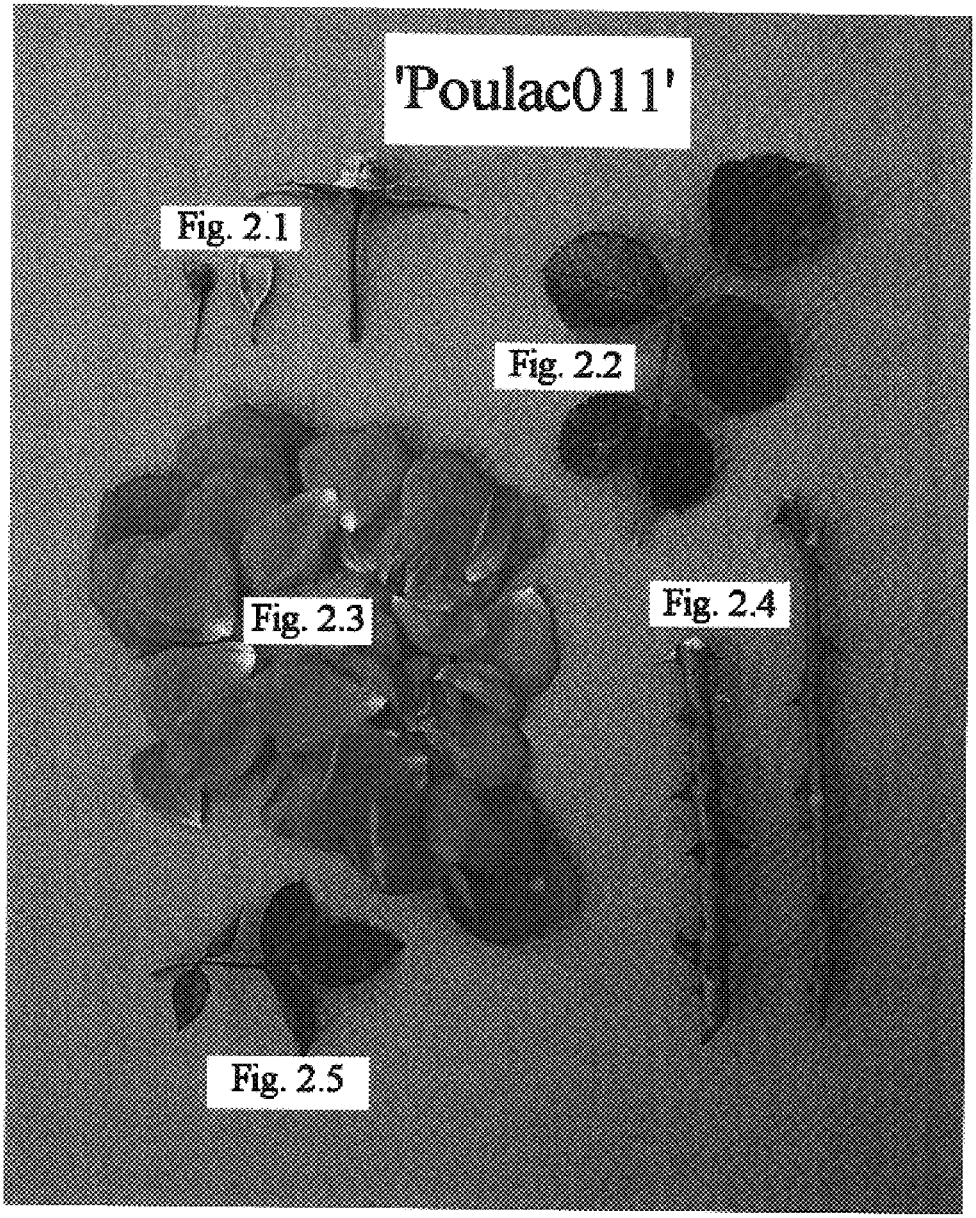
'Poulac011'
Fig. 2.1
Fig. 2.2
Fig. 2.3
Fig. 2.4
Fig. 2.5

UNITED STATES PATENT AND TRADEMARK OFFICE

CERTIFICATE OF CORRECTION

PATENT NO. : PP 15,821 P2
DATED : June 28, 2005
INVENTOR(S) : L. Pernille Olesen and Mogens N. Olesen It is certified that error appears in the above-identified patent and that said Letters Patent is hereby corrected as shown below:

Title page,
Item [54], Title, should read:
-- COMPACT FLORIBUNDA ROSE PLANT NAMED `POULAC011' --.

Signed and Sealed this

Seventh Day of February, 2006

JON W. DUDAS
*Director of the United States Patent and Trademark Office*